(12) United States Patent
Zhao et al.

(10) Patent No.: US 11,771,721 B2
(45) Date of Patent: Oct. 3, 2023

(54) APPLICATIONS OF GENETICALLY ENGINEERED BACTERIA VNP20009-M IN PREPARATION OF DRUGS FOR PREVENTING AND TREATING LUNG CANCER

(71) Applicant: GUANGZHOU SINOGEN PHARMACEUTICAL CO., LTD, Guangzhou (CN)

(72) Inventors: Allan Zijian Zhao, Guangzhou (CN); Yan Lin, Guangzhou (CN); Sujin Zhou, Guangzhou (CN); Fanghong Li, Guangzhou (CN)

(73) Assignee: GUANGZHOU SINOGEN PHARMACEUTICAL CO., LTD, Guangzhou (CN)

( * ) Notice: Subject to any disclaimer, the term of this patent is extended or adjusted under 35 U.S.C. 154(b) by 509 days.

(21) Appl. No.: 16/497,820

(22) PCT Filed: Mar. 29, 2018

(86) PCT No.: PCT/CN2018/081115
§ 371 (c)(1),
(2) Date: Sep. 26, 2019

(87) PCT Pub. No.: WO2018/177374
PCT Pub. Date: Oct. 4, 2018

(65) Prior Publication Data
US 2020/0023019 A1    Jan. 23, 2020

(30) Foreign Application Priority Data
Apr. 1, 2017    (CN) .......................... 201710213446.6

(51) Int. Cl.
*A61K 35/74*    (2015.01)
*A61P 35/00*    (2006.01)
*A61K 9/00*    (2006.01)
*C12N 15/74*    (2006.01)
*C12N 1/20*    (2006.01)
*C12R 1/42*    (2006.01)

(52) U.S. Cl.
CPC ............ *A61K 35/74* (2013.01); *A61K 9/0019* (2013.01); *A61P 35/00* (2018.01); *C12N 1/205* (2021.05); *C12N 15/74* (2013.01); *C12R 2001/42* (2021.05)

(58) Field of Classification Search
None
See application file for complete search history.

(56) References Cited

U.S. PATENT DOCUMENTS

| | | |
|---|---|---|
| 2015/0376593 A1 | 12/2015 | Lin et al. |
| 2018/0008682 A1 | 1/2018 | Zhao et al. |
| 2018/0339032 A1 | 11/2018 | Zhao et al. |
| 2020/0023019 A1 | 1/2020 | Zhao et al. |

FOREIGN PATENT DOCUMENTS

CN    105983103    * 10/2016

OTHER PUBLICATIONS

English translation; WO2016/145974, 2016.*
Kosaki et al (Cancer Research 69:2535-2540, 2000).*
He et al., (2007, Proc. Intl. Soc. Mag. Reson. Med. 15:2836).*
English translation of CN 105983103 15 pages, 2016.*
Yang Da-Yun et al., "Expression and Significance of R KIP and EZH2 in non—small cell lung cancer", Modern Preventive Medicine, 2016, vol. 43, No. 10, p. 1910-1914.
English translation of the International Search Report for International Application No. PCT/CN2018/081115, 2018.

* cited by examiner

*Primary Examiner* — Patricia Duffy
(74) *Attorney, Agent, or Firm* — Jun He Law Offices P.C.; Yi Zhang

(57) ABSTRACT

Provided is application of genetically engineered bacteria VNP20009-M in preparation of drugs for preventing and treating lung cancer.

11 Claims, 9 Drawing Sheets

APPLICATIONS OF GENETICALLY ENGINEERED BACTERIA VNP20009-M IN PREPARATION OF DRUGS FOR PREVENTING AND TREATING LUNG CANCER

CROSS-REFERENCE TO RELATED APPLICATIONS

The present application is the national phase of International Application PCT/CN2018/081115, filed Mar. 29, 2018, which claims the benefit of Chinese Patent Application No. CN 201710213446.6, filed Apr. 1, 2017, the disclosure of which is incorporated herein by reference in the entirety.

FIELD OF THE INVENTION

The present invention belongs to the technical field of genetic engineering drugs and particularly relates to new application of genetically engineered bacteria VNP20009-M in preparation of drugs for preventing and treating lung cancer.

BACKGROUND

Cancers have become an important cause of human death with cancer incidence rates increasing by 33% from 2005 to 2015. The World Cancer Report 2014 published by the World Health Organization (WHO) predicts a rapid increase in world cancer cases, from 14 million in 2012 to 19 million in 2025 year by year and reaching 24 million by 2035.

Among the cancers, lung cancer is one of the most malignant tumors, threatening people's health and life. The incidence rate and mortality rate are the highest. In 2012 alone, almost 1.6 million people worldwide died of lung cancer. The 2015 Annual Report of the Cancer Registration Center of China shows that the incidence rate and the mortality rate of lung cancer are also the highest in China. There are more than 700,000 new cases of lung cancer in China and the death toll is more than 600,000. Most patients with lung cancer are discovered late and only adapted for drug treatment. Traditional treatments for lung cancer include local treatments (including surgery, radiotherapy, etc.) and systemic treatments (including traditional chemotherapy, molecular targeted drug therapy, etc.). Although modern medical researches have made great progress, many targeted drugs such as gefitinib, erlotinib, etc. have been invented, and lung cancer has made some progress in the radiotherapy, chemotherapy and surgery, the overall prognosis is still poor. According to statistics in 2015, the 5-year survival rate of patients with lung cancer in China is only 16.1%. Therefore, finding new ways to treat lung cancer has become a problem that scientists need to solve urgently.

The prior art shows that methionine dependence is a characteristic of most tumor cells, which is manifested by excessive demands for methionine by the tumor cells and cell proliferation is inhibited when culture is conducted in a methionine removed or precursor homocysteine substituted culture medium; while in the presence of the methionine, the cells can grow normally, including more than ten malignant tumor cells of prostate cancer, breast cancer, lung cancer, etc. However, there is no methionine dependence in normal cells. The method that causes methionine deficiency mainly includes removing the methionine from diet or decomposing the methionine by using methioninase. However, limiting intake of the methionine in diet alone has a limited effect on lowering the methionine level, and long-term limiting on the methionine intake can cause body malnutrition and metabolic disorders. Compared to the diet-limited methionine intake, the use of the methioninase does not cause excessive metabolic problems and has an anti-tumor effect.

*Salmonella* is a group of Gram-negative and invasive intracellular facultative anaerobic bacteria parasitized in intestines of humans and animals. Among the *salmonella*, a known bacterium strain VNP20009 is a vector with high tumor targeting properties, safety, and antitumor effects. The VNP20009 has significant tumor growth inhibition effects on various mouse solid tumor models of malignant melanoma, lung cancer, etc. Two phase I clinical studies conducted in the United States show that the VNP20009 can be used in the human body, has safety, but shows no antitumor effects.

SUMMARY

To this end, a technical problem to be solved by the present invention is to provide new application of genetically engineered bacteria VNP20009-M in preparation of drugs for preventing and treating lung cancer.

In order to solve the above technical problem, the present invention discloses the application of the genetically engineered bacteria VNP20009-M in the preparation of the drugs for preventing and treating the lung cancer.

Further, the lung cancer includes lung primary tumor, recurrent tumor after lung cancer surgery and lung cancer metastatic tumor.

Further, the lung cancer includes non-small cell lung cancer, small cell lung cancer, etc.

Non-small cell lung cancer, a major type of lung cancer originating from epithelial cells, includes squamous carcinoma, adenocarcinoma, adenosquamous carcinoma, large cell lung cancer or undifferentiated carcinoma.

Squamous carcinoma is the most common type of the lung cancer, accounting for about 50%. A majority of the patients are more than 50 years old, and males are the majority. Most of the squamous carcinoma originate from larger bronchus, often are central type lung cancer, and less sensitive to radiotherapy and chemotherapy than that of the undifferentiated carcinoma.

Adenocarcinoma, which is relatively common in females, originates from bronchial mucosa epithelium, with a small number of the adenocarcinoma originating from mucous glands of large bronchus. There are no obvious clinical symptoms in an early stage. Local infiltration or hematogenous metastasis can occur when the adenocarcinoma is discovered. The adenocarcinoma easily metastasizes to organs of liver, brain, bones, etc. in clinical practice and may also involve pleura to cause pleural effusion. The adenocarcinoma is less sensitive to radiation therapy.

Adenosquamous carcinoma and large cell carcinoma have a high degree of malignancy and a low degree of differentiation, and are prone to brain metastasis, poor in therapeutic effects and poor in prognosis. At present, treatments of large cell lung cancer are mainly based on comprehensive treatments in clinical practice, and the effect of simple surgery or radiotherapy and chemotherapy is poor.

Undifferentiated carcinoma, common in malee, has an incidence rate ranking only second to the squamous carcinoma. Onset at early age, undifferentiated carcinoma has a high degree of malignancy and grows fast. Undifferentiated carcinoma shows wide range lymphatic and hematogenous metastasis at relatively early stage. Undifferentiated carcinoma is relatively sensitive to radiotherapy and chemotherapy and has the worst prognosis in various types of lung cancer.

Small cell carcinoma, also known as small cell neuroendocrine carcinoma, is the most malignant type of lung cancer. Small cell carcinoma grows fast and metastasizes early, often to organs of brain, liver, bones, adrenal gland, etc. Commonly having a survival period of less than one year, small cell carcinoma is hard to remove by surgical resection but sensitive to radiotherapy and chemotherapy. However, radiotherapy and chemotherapy are often accompanied with strong toxic and side effects as well as complications, showing a relatively poor prognosis.

Preferably, the genetically engineered bacteria VNP20009-M have a minimum effective administration dose of $3.5*10^7$ CFU/M$^2$.

The genetically engineered bacteria VNP20009-M used for cancer prevention and treatment can be administered by various routes including but not limited to oral administration, local administration, injection administration (including but not limited to transvenous, peritoneal, subcutaneous, intramuscular, intratumoral administrations), etc.

The present invention also discloses application of the genetically engineered bacteria VNP20009-M in preparation of a methioninase agent. The genetically engineered bacteria VNP20009-M have relatively high methioninase activity and can be used for the preparation of the methioninase agent.

The methioninase agent can be administered by various routes including but not limited to oral administration, local administration, injection administration (including but not limited to transvenous, peritoneal, subcutaneous, intramuscular, intratumoral administrations), etc.

As known in the prior art, the genetically engineered bacterium VNP20009-M of the invention is a known bacterium strain, whose properties, shapes, and construction methods have been described in Chinese Patent No. CN105983103A.

The genetically engineered bacterium VNP20009-M is attenuated *Salmonella typhimurium* VNP20009 cloned with a L-methioninase gene.

Further, the genetically engineered bacterium VNP20009-M is attenuated *Salmonella typhimurium* VNP20009 carrying a plasmid, wherein the plasmid is cloned with the L-methioninase gene.

The plasmid includes but is not limited to a pSVSPORT plasmid, a pTrc99A plasmid, a pcDNA3.1 plasmid, a pBR322 plasmid or a pET23a plasmid.

The genetically engineered bacterium VNP20009-M is constructed by subcloning the L-methioninase gene into the plasmid to obtain L-methioninase expression plasmid, and electrotransforming the L-methioninase expression plasmid into the attenuated *Salmonella typhimurium* VNP20009.

Most preferably, in the construction process of the genetically engineered bacterium VNP20009-M, when the pSVSPORT plasmid is selected, the L-methioninase gene is subcloned into the plasmid to obtain the L-methioninase expression plasmid, and then the L-methioninase expression plasmid is electrotransformed into the attenuated *Salmonella typhimurium* VNP20009 to obtain the genetically engineered bacterium.

Wherein, electrotransformation is conducted under a voltage of 2,400 V, a resistance of 400Ω, a capacitance of 25 μF and a discharge time of 4 ms.

The present invention discloses the new application of the genetically engineered bacterium VNP20009-M for treating the lung cancer on the existing basis, the genetically engineered bacterium VNP20009-M can effectively kill lung cancer tumor cells, eliminate lung cancer tumor lesions, and have better killing effects and better therapeutic effects for primary lung cancer, recurrent lung cancer after surgery and lung cancer metastasized tumor cells to other sites; and besides, the genetically engineered bacterium has no obvious toxic and side effects on the human body and provide safe and effective new methods for the treatment of lung cancer.

BRIEF DESCRIPTION OF THE DRAWINGS

In order to make the content of the present invention easier to understand, the present invention will be further described in detail below with reference to the embodiments of the present invention accompanying with the drawings, wherein.

DETAILED DESCRIPTION

Example 1 Construction of Genetically Engineered Bacteria VNP20009-M

The construction method and processes of the genetically engineered bacterium VNP20009-M of the present invention are described in the examples of the Chinese Patent No. CN105983103A.

(1) Construction of Plasmid Expressing L-Methioninase Gene

The L-methioninase (GenBank: L43133.1) gene was synthesized and subcloned into a pUC57 plasmid (GenScript). The pUC57 plasmid subcloned with the L-methioninase gene was then subcloned into a pSVSPORT plasmid (Invitrogen) by Kpn I and Hind III enzyme cutting sites to obtain a pSVSPORT-L-methioninase expression plasmid. The specific construction processes are as follows:

the pSVSPORT plasmid was subjected to Kpn I and Hind III double enzyme cutting. An enzyme cutting system contained 2 μg of plasmid DNA, 3 μL of 10*buffer, 1.5 μL of Kpn I enzyme, 1.5 μL of Hind III enzyme, and ddH$_2$O added to supplement sufficiently a volume to 30 μL, and incubated in warm bath at 37° C. for 3 h. Then the enzyme cutting system was separated by electrophoresis in 1% agarose gel. A DNA band of 4.1 kb was cut out and purified by a gel recovery and purification kit.

The DNA fragment of a L-methioninase coding region was obtained by whole-gene synthesis. The obtained DNA fragment was subcloned into the pUC57 plasmid (GenScript). The pUC57 plasmid subcloned with the DNA fragment was subjected to the Kpn I and Hind III double enzyme cutting using an enzyme cutting system containing 3 μg of plasmid DNA, 3 μL of 10*buffer, 1.5 μL of Kpn I enzyme, 1.5 μL of Hind III enzyme, and ddH$_2$O added to supplement sufficiently a volume to 30 μL, which was incubated in warm bath at 37° C. for 3 h. The enzyme cutting system was then separated by electrophoresis in 1% agarose gel. A DNA band of 1.2 kb was cut out and purified by a gel recovery and purification kit.

The pSVSPORT (Kpn I/Hind III) and the DNA fragment of the L-methioninase coding region (Kpn I/Hind III) were ligated with a ligation reaction containing 2 μL of the vector, 6 μL of the inserting fragments and 1 μL of T4 DNA ligase and incubated in warm bath at 16° C. for 16 h.

The ligation product was transformed into competent cells of *E. coli* DH5a (Takara). A tube of 50 μL of DH5a competent cells was placed on ice. After the ice was melt, 5 μL of the above-mentioned ligation product was added into the DH5a competent cells with slight flipping to mix. The mixture was incubated on ice for 30 min before heat shock at 42° C. for 60 s and then incubated on ice for 2 min. 500 μL of LB liquid medium without antibiotics was added to the mixture and incubated at 37° C. for 1 h with shaking, after which the material was spread on an ampicillin-containing LB culture medium plate and cultured overnight.

Figure 1:
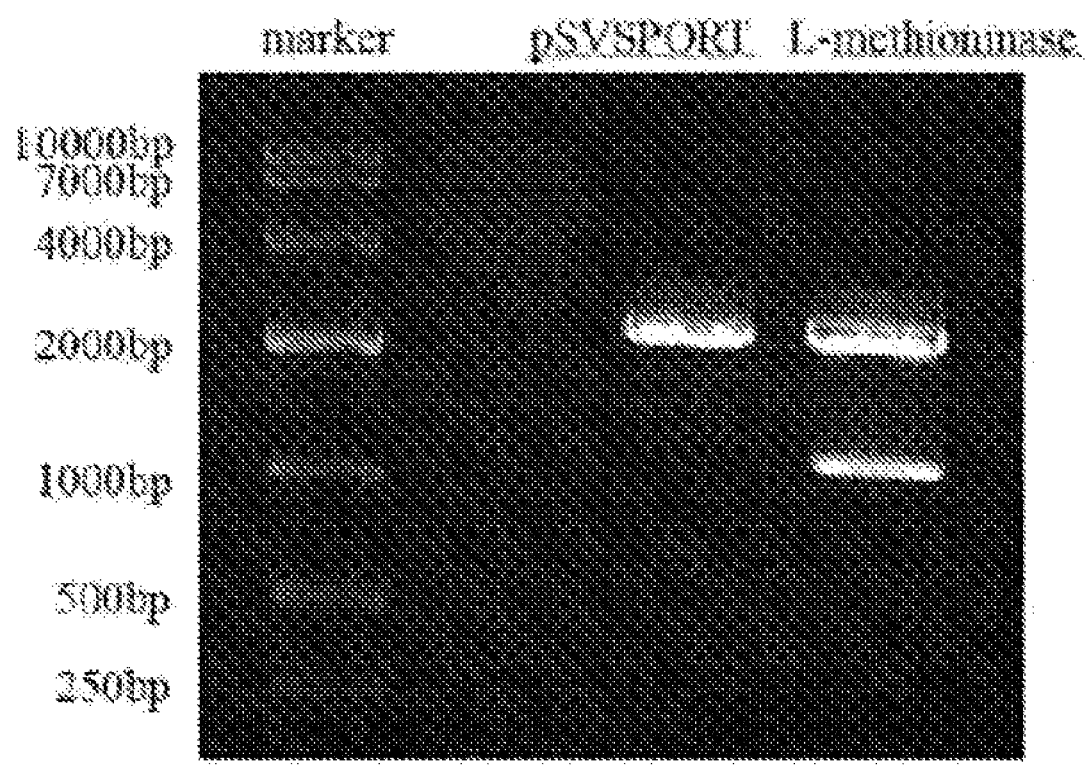
FIG. 1 is a diagram of 1% agarose gel electrophoresis to identify the plasmid pSVSPORT-L-methioninase by enzyme digestion.

After clones were grown, single colonies were picked into 3 mL of ampicillin-containing LB culture liquid, incubated in a shaker at 37° C. for 16 h. Plasmid DNA was extracted and identified by Kpn 1 and Hind 111 enzyme digestion. As shown in FIG. 1, the positive clone had two DNA bands of 4.1 kb and 1.2 kb. Sequencing confirmed that the sequences of the positive clones are completely correct.

(2) Constructions of VNP20009 Bacterium Carrying a Plasmid and VNP20009 Bacterium Carrying a Plasmid Cloned with a L-Methioninase Gene pSVSPORT and pSVSPORT-L-methioninase expression plasmids were respectively electrotransformed into the VNP20009 bacterium strain (YS1646, ATCC No. 202165) which were respectively named as VNP20009-V and VNP20009-M. The specific construction processes are as follows:

Competent bacteria VNP20009 were placed on ice, after the ice was melted, the competent bacteria VNP20009 were transferred to a pre-cooled electric rotating cup, 2 μL of the plasmid was added into the electric rotating cup, slight flipping and uniform mixing were conducted, and incubation was conducted on ice for 1 min. The electric rotating cup was put into an electric rotating instrument, and conditions were set as a voltage of 2,400 V, a resistance of 400Ω, a capacitance of 25 μF and a discharge time of 4 ms. 1 mL of a SOC culture medium was added immediately after electric shock, and gentle and even mixing was conducted. Shaking culture is conducted at 37° C. for 1 h; and after a pipettor was used to precipitate and blow the bacteria evenly, the bacteria were applied on an ampicillin-containing resistant LB-O culture medium plate. The plate was then put in an incubator for culture at 37° C. for 16 h. After the VNP20009-V and VNP20009-M were cultured with the LB-O, the plasmid was extracted and identified by enzyme cutting to be correct.

Figure 2:
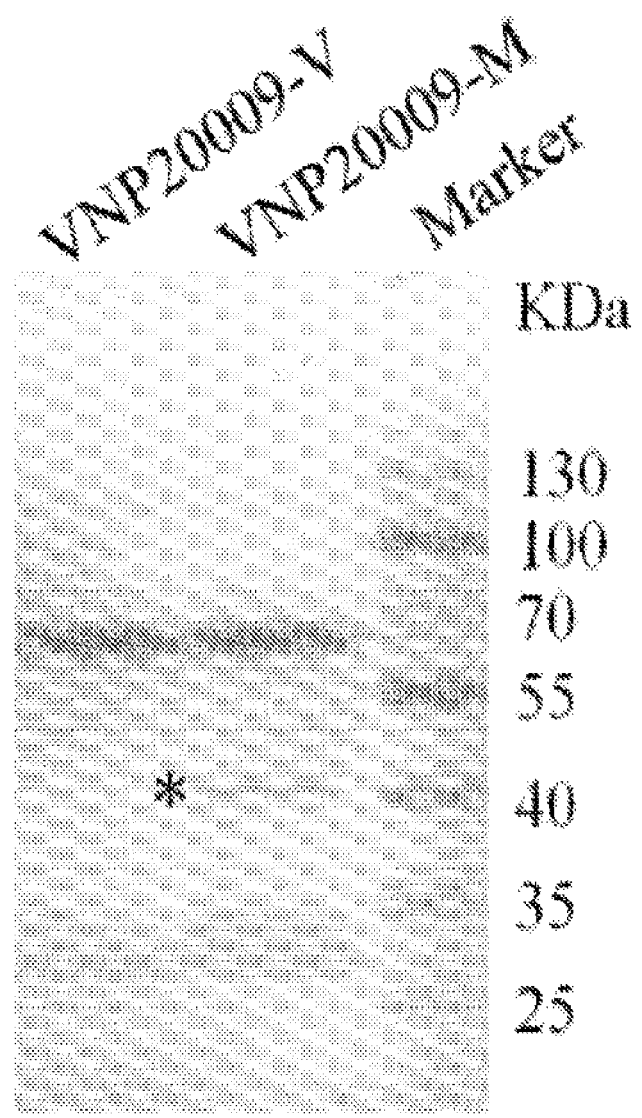
FIG. 2 is a diagram showing results of methioninase expression identified by Western blot according to the present invention.

$1 \times 10^8$ of *salmonella* were taken, proteins were extracted by a protein lysate, 10% SDS-PAGE electrophoresis was conducted, then electrotransformation to a PVDF membrane in an ice bath under stable pressure was conducted, after BSA room temperature sealing was conducted for 1 h, TBST rinsing was conducted for 3*5 min, a rabbit anti-L-methioninase antibody was added (1:1000), and incubation was conducted overnight at 4° C. The TBST rinsing was conducted for 3 times with 5 min each time, then a HRP-labeled anti-rabbit secondary antibody (1:10000) was added, incubation was conducted at room temperature for 1 h, the TBST rinsing was conducted for 3 times with 5 min each time, and ECL chemiluminescence developing was conducted. The results are shown in FIG. 2, a specific band was observed at a molecular weight of about 43 kD, indicating that the expression level of the L-methioninase was significantly increased in the VNP20009-M compared with the VNP20009 and VNP20009-V.

Figure 3:
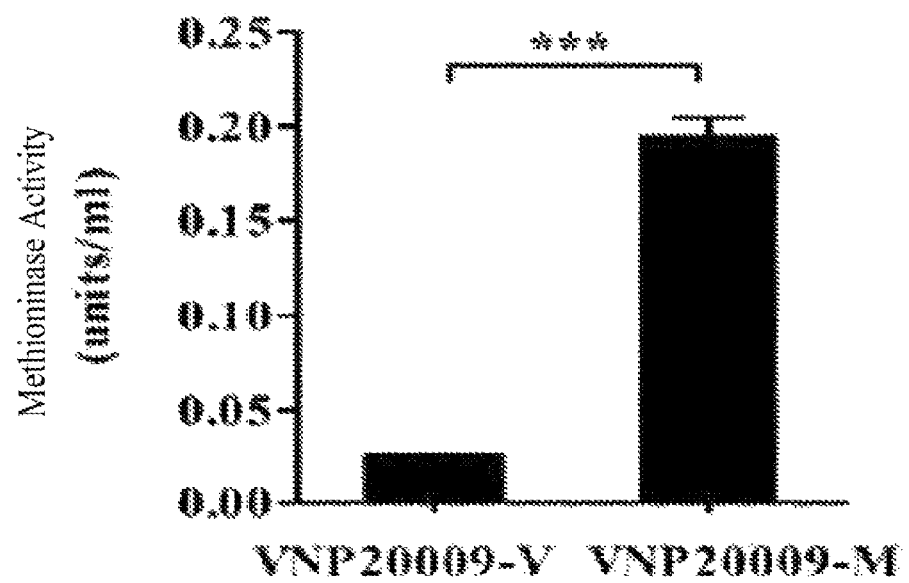
FIG. 3 is a diagram showing the results of detecting methioninase activity in *salmonella* according to the present invention.

L-methionine and pyridoxal were respectively mixed with the VNP20009-V and VNP20009-M bacteria. After incubation was conducted at 37° C. for 10 min, termination was conducted with 50% trichloroacetic acid, centrifugation was conducted, a supernatant was taken, the supernatant was mixed fully and evenly with 3-methyl-2-benzothiazolinone hydrazone hydrochloride hydrate (MBTH), after incubation was conducted at 50° C. for 30 min, absorbance at 320 nm was measured, and the amount of enzyme used for catalytic conversion of 1 μmol of α-ketobutyric acid per minute was defined as 1 enzyme activity unit. The results show (as shown in FIG. 3) that the activity of the methioninase in the *salmonella* VNP20009-M was 10 times higher than that of VNP20009-V.

Thus, the constructed genetically engineered *salmonella* VNP20009-M has a relatively high methioninase activity and can be used for preparation of a methioninase agent.

Example 2 Antitumor Effect of Genetically Engineered Bacterium VNP20009-M

1) Past Medical History and Diagnosis

Figure 4:
FIG. 4 shows a condition of new lesions in the neck of the patient in Example 2.
Figure 5:
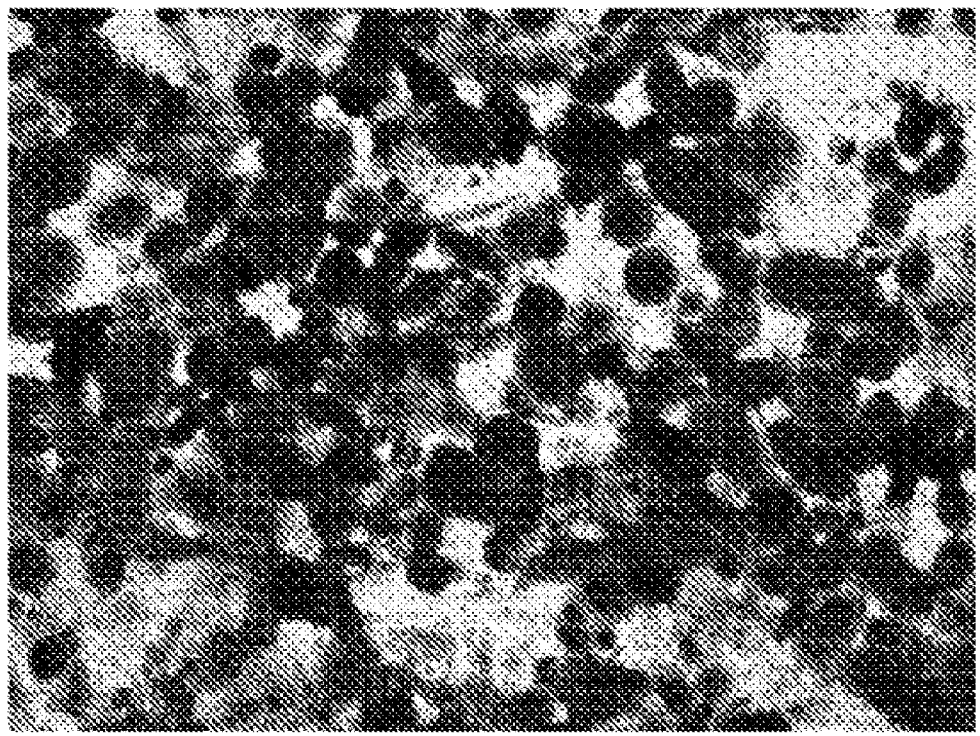
FIG. 5 shows a biopsy cell smear of the patient's tumor in Example 2.

After a 73 years old male patient underwent a thoracoscopic right lung lower lobe squamous cell carcinoma radical operation for 5 months, a new mass was found in the neck (as shown in FIG. 4). The size of the lesion mass at the neck was measured as about 8 cm*9 cm. Cancer cells were identified by a cell smear from the lesion site biopsy (as shown in FIG. 5). In addition, a bone ECT showed multiple active bone metabolism; and a chest CT examination report showed sternal destruction with mass formation.

According to the previous treatments and related examinations, the patient was diagnosed as recurrence and metastasis after the right lung lower lobe squamous cell carcinoma operation, but there was no standard treatment plan in clinic.

2) Treatment Plan

The diluted VNP20009-M was evenly injected into the tumor site in multi-points and during the first time, $6*10^7$ cfu (about $3.5*10^7$ cfu/m$^2$) of the VNP20009-M was administered. After a one-week interval, a second administration was conducted and a total amount of the drug was increased to $9*10^7$ cfu (about $5*10^7$ cfu/m$^2$). An intratumoral injection was conducted by even and multi-point drug injection. After a one-week interval, a third administration was conducted with the same method and dose as in the 2$^{nd}$ administration. After a 10-day interval, a fourth administration was conducted. The drug concentration was increased to $6*10^7$ cfu/m$^2$, and the intratumoral administration was conducted. After a 10-day interval, a fifth administration was conducted with the same method and dose as the 4th administration. A specific implementation plan is shown in Table 1 below.

TABLE 1

Treatment implementation plan

| Times | Time | Dose |
|---|---|---|
| $1^{st}$ | 0 day | $3.5*10^7$ cfu/m$^2$ |
| $2^{nd}$ | $7^{th}$ day | $5*10^7$ cfu/m$^2$ |
| $3^{rd}$ | $14^{th}$ day | $5*10^7$ cfu/m$^2$ |
| $4^{th}$ | $24^{th}$ day | $6*10^7$ cfu/m$^2$ |
| $5^{th}$ | $34^{th}$ day | $6*10^7$ cfu/m$^2$ |

3) Efficacy
3.1 Changes of Lesion Sizes

Figure 6:
FIG. 6 shows a condition of the tumor of the patient after 3 weeks of treatment in Example 2.
Figure 7:
FIG. 7 shows a condition of the mass of the patient after 5 weeks of treatment in Example 2.
Figure 8:
FIG. 8 shows a condition of the original lesion site of the patient after 12 weeks of treatment in Example 2.

The size of the lesion mass at the neck was measured to be approximately 8 cm*9 cm before the treatment (as shown in FIG. 4). After 3 weeks of the treatment, the mass was significantly reduced (as shown in FIG. 6). After 5 weeks of the treatment (the end of the 5-times treatments), the mass basically disappeared (as shown in FIG. 7). After 12 weeks of the treatment, there was no abnormal change in the neck clavicle, i.e., the original lesion site (as shown in FIG. 8).

3.2 Changes Inside the Tumor

Before the treatment, the inside of the mass was of a cystic structure. And more severely abnormal-shaped cells, i.e., tumor cells were found by a cytological smear analysis (as shown in FIG. 5).

Figure 9:
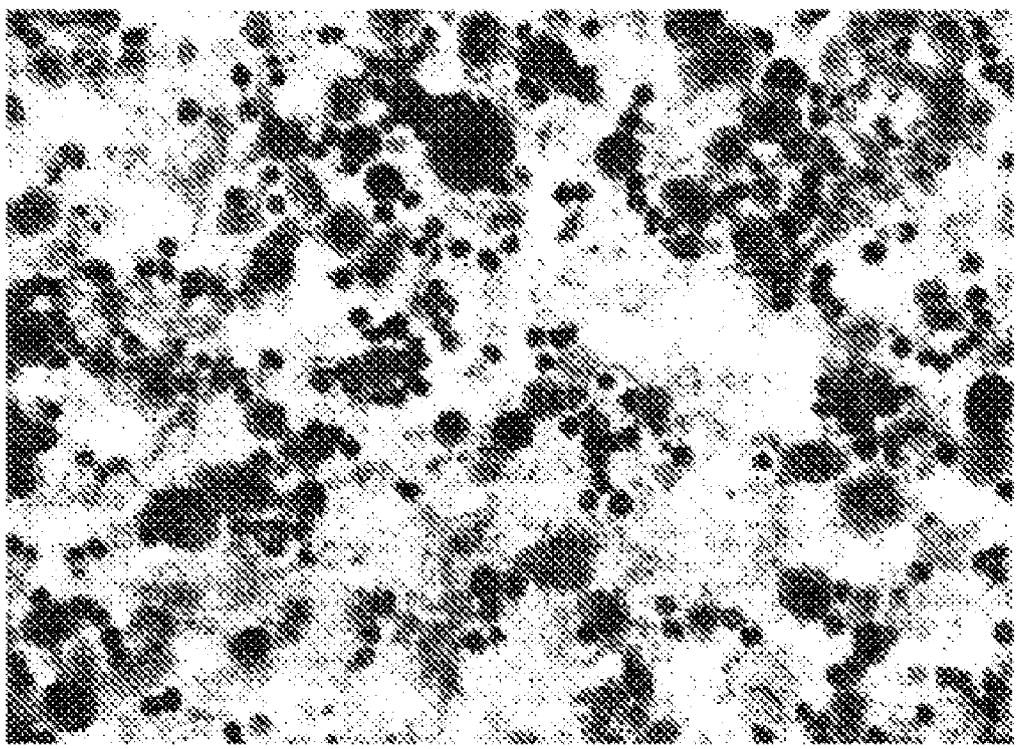
FIG. 9 is a cytological smear of the patient's tumor after 1 week of treatment in Example 2.
Figure 10:
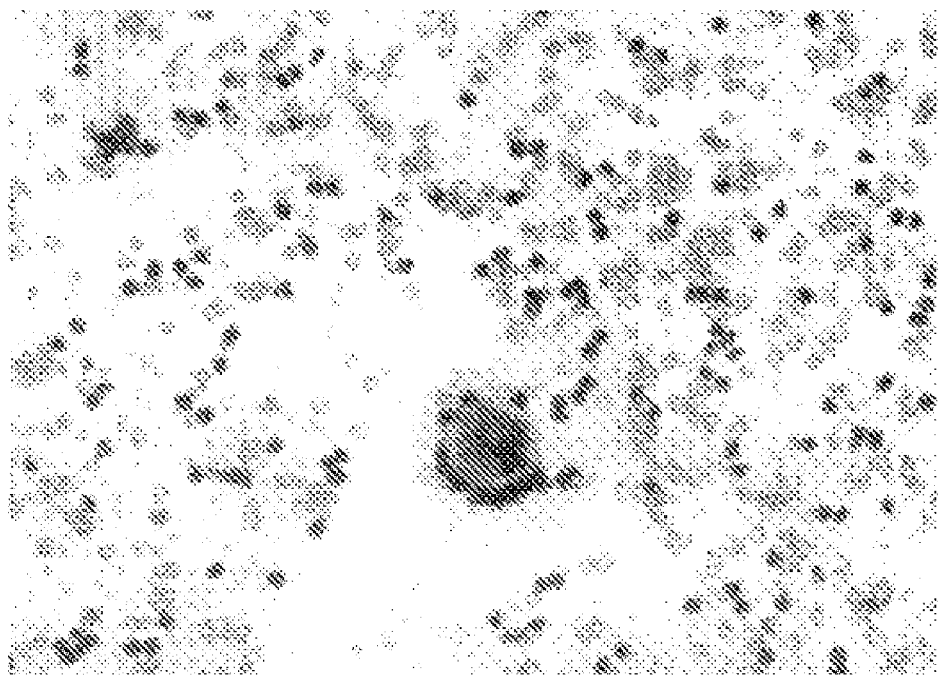
FIG. 10 is a cytological smear of the patient's tumor after 3 weeks of treatment in Example 2.

One week after the treatment (one administration), the mass was significantly softened (as shown in FIG. 9). A large number of neutrophils and a small number of tumor cells were found by a cytological smear. Ten days after the treatment (with two administrations), about 40 mL of effusion was extracted. Two weeks after the treatment (twice treatment), the inside of the mass was further liquefied and about 90 mL of the effusion was extracted. Three weeks after the treatment (with three administrations), the tumor was shrunk (as shown in FIG. 10). About 45 mL of the effusion was continuously extracted. A large number of inflammatory cells and a very small number of tumor cells were found by a cytological smear. It was observed that the inflammatory cells wrapped around the periphery of the tumor cells. One month after the treatment (with four administrations), the tumor was further reduced; and the extracted effusion was reduced to about 20 mL. After the end of the fifth administration, no effusion was detected, and the mass was eliminated.

The above results indicate that the injection of the genetically engineered bacteria VNP20009-M of the present invention into the inside of the tumor lesion induced local inflammatory cell infiltration, thereby killing the tumor cells.

3.3 Side Effects

On the day of each administration and 9-10 hours after the injection, the patient had a fever of about 38° C. and restored to normal body temperature by physical cooling. On the day of administration, nausea and vomiting sometimes occurred for about 10 minutes. Other than that, there was no abnormal feeling. During the treatment, various indicators of liver and kidney functions were examined; and the results are shown in Table 2 below. The results show that the various indicators of the liver and kidney functions of the patient are all in the normal range. The above results indicate that the VNP20009-M has no obvious toxicity to the human body.

TABLE 2

Results of various examination indicators of the patient

| Indicators | Before the treatment | 1 week after the treatment | 2 weeks after the treatment | 5 weeks after the treatment | 12 weeks after the treatment | Reference value |
|---|---|---|---|---|---|---|
| Alanine aminotransferase | 22.1 | 25.9 | 38.7 | 23.3 | 18.1 | 0-60.0 U/L |
| Aspartate aminotransferase | 14.2 | 13.8 | 16 | 16.2 | 15 | 0-40.0 U/L |
| Total bilirubin | 10.22 | 7.98 | 8.52 | 8.68 | 11.14 | 2.00-20.50 µmol/L |
| Alkaline phosphatase | 98.3 | 74.2 | 100.8 | 110.9 | 108.3 | 45-125 U/L |
| Albumin | 36.6 | 35.5 | 37.18 | 39.8 | 44.2 | 40.00-55.00 g/L |
| Urea | 4.78 | 3.65 | 4.93 | 5.84 | 4.75 | 1.70-8.30 mmol/L |
| Creatinine | 61 | 65.2 | 48 | 48.8 | 53.7 | 42.0-104.0 µmol/L |
| Blood platelet | 352 | 361 | 406 | 296 | 281 | 100-300 10 * 9/L |
| Sodium | 132 | 130.3 | 134.6 | 133 | 135 | 137-147 mmol/L |

The above data prove that the genetically engineered bacterium VNP20009-M of the present invention can treat lung cancer, effectively killing the lung squamous cancer cells and eliminating the tumor lesions, and having no obvious toxic and side effects on the human body.

It is apparent that the above-described examples are merely illustrative and are not intended to limit the invention. Other variations or modifications of the various forms may also be made by those of ordinary skill in the art in light of the above description. There is no need and no way to exhaust all of the embodiments. And the obvious variations or modifications derived therefrom are still in the protection scope created by the present invention.

The invention claimed is:

1. A method for treating lung cancer, the method comprising administering a therapeutically effective amount of genetically engineered bacterium to a human having lung cancer, wherein the genetically engineered bacterium is attenuated *Salmonella typhimurium* VNP20009 cloned with a L-methioninase gene.

2. The method of claim 1, wherein the lung cancer is a primary lung tumor, a recurrent tumor after lung cancer surgery or a metastatic tumor from lung cancer.

3. The method of claim 1, wherein the lung cancer is non-small lung cancer or small cell lung cancer.

4. The method of claim 3, wherein the non-small cell lung cancer is squamous carcinoma, adenocarcinoma, adenosquamous carcinoma, large cell lung cancer or undifferentiated carcinoma.

5. The method of claim 1, wherein the genetically engineered bacterium is administered at a dose of at least $3.5 \times 10^7$ CFU/M$^2$.

6. The method of claim 1, wherein the genetically engineered bacterium is administered once a week.

7. The method of claim 1, wherein the genetically engineered bacterium is administered orally, locally or via injection.

8. The method of claim 7, wherein the genetically engineered bacterium is administered via intratumoral injection.

9. The method of claim 1, wherein the genetically engineered bacterium carries a plasmid which is cloned with the L-methioninase gene.

10. The method of claim 1, wherein the plasmid is a pSVSPORT plasmid, a pTrc99A plasmid, a pcDNA3.1 plasmid, a pBR322 plasmid or a pET23a plasmid.

11. The method of claim 1, wherein the genetically engineered bacterium is constructed by: subcloing the L-methioninase gene into the plasmid, then electro-transforming the plasmid to attenuated *Salmonella typhimurium* VNP20009.

* * * * *